United States Patent [19]

Beuther et al.

[11] 4,420,930
[45] Dec. 20, 1983

[54] PROCESS FOR OPERATING A FURNACE OR A COMBUSTION ENGINE

[75] Inventors: Harold Beuther, Cheswick; Johan G. Schulz, Pittsburgh, both of Pa.

[73] Assignee: Gulf Research & Development Company, Pittsburgh, Pa.

[21] Appl. No.: 232,997

[22] Filed: Feb. 9, 1981

Related U.S. Application Data

[63] Continuation-in-part of Ser. No. 46,442, Jun. 7, 1979, Pat. No. 4,278,443.

[51] Int. Cl.³ .............................................. F02C 3/20
[52] U.S. Cl. .................................... 60/39.461; 44/53; 44/56; 110/347; 123/1 A; 123/198 A; 208/8 LE
[58] Field of Search ................. 44/53, 56; 208/8 LE; 585/3, 14; 123/1 A, 198 A; 60/39.461; 110/347

[56] References Cited

U.S. PATENT DOCUMENTS

| | | | |
|---|---|---|---|
| 3,120,474 | 2/1964 | Gorin et al. | 208/8 LE |
| 4,096,658 | 5/1978 | Bay | 44/53 |
| 4,124,485 | 11/1978 | Carr et al. | 208/8 LE |
| 4,192,240 | 6/1979 | Malek | 208/8 LE |
| 4,210,103 | 7/1980 | Dimitroff | 123/1 A |

OTHER PUBLICATIONS

"Characteristics of Products Obtained by Oxidation of Anthracite with Concentrated Nitric Acid", RI Bureau of Mines Report of Investigation 6535, Kersten et al., U.S. Dept. of Interior, Bureau of Mines, 1964, pp. 1–11.
"The Use of Solvents in Synthetic Organic Chemistry", MacArdle, 1925, p. 50, 1st full paragraph.

*Primary Examiner*—Anton H. Sutto
*Assistant Examiner*—Mrs. Y. Harris-Smith
*Attorney, Agent, or Firm*—Deane E. Keith; Forrest D. Stine; Joseph J. Carducci

[57] ABSTRACT

Process for operating a furnace or a combustion engine which comprises burning in said furnace or said combustion engine a mixture of polycyclic, polycarboxylic acids obtained by oxidizing coal with aqueous nitric acid, separating from the resulting product an aqueous phase and a solid phase and then extracting the solid phase with a solvent to recover said mixture.

27 Claims, No Drawings

PROCESS FOR OPERATING A FURNACE OR A COMBUSTION ENGINE

This application is a continuation-in-part application of our application Ser. No. 46,442 for ENERGY GENERATING PROCESS AND NOVEL FUEL THEREFOR, filed June 7, 1979, now U.S. Pat. No. 4,278,443.

BACKGROUND OF THE INVENTION

1. Field of the Invention

This invention relates to a process for operating a furnace of a combustion engine which comprises burning in said furnace or said combustion engine a mixture of polycyclic, polycarboxylic acids obtained by oxidizing coal with aqueous nitric acid, separating from resulting product an aqueous phase and a solid phase and then extracting the solid phase with a solvent to recover said mixture.

2. Description of the Prior Art

Ash (inorganic components which will not burn) can be removed from coal by heating a coal slurry with hydrogen at elevated temperatures and elevated pressures for a time sufficient to liquefy the coal and then subjecting the the hydrogenated product to filtration to remove the solids (ash) therefrom. Although the process is effective for its intended purpose the cost is high because of the large amounts of hydrogen consumed and because of the high temperatures and high pressures required. It would be highly desirable, therefore, to find an alternative process for deashing coal, particularly with coals that are to be burned in a furnace or a combustion engine.

SUMMARY OF THE INVENTION

We have discovered a process for operating a furnace of a combustion engine which comprises burning in said furnace or said combustion engine a mixture of polycyclic, polycarboxylic acids obtained by oxidizing coal with aqueous nitric acid, separating from the resulting product an aqueous phase and a solid phase and then extracting the solid phase with a solvent to recover said mixture. The mixture of polycyclic, polycarboxylic acids recovered following the defined procedure can be used as such or it can be employed in the form of a novel composition comprising such mixture of polycyclic, polycarboxylic acids and methanol, ethanol, normal propanol or isopropanol or one comprising such mixture and a known hydrocarbon fuel.

Raw coal that can be used to prepare the mixture of polycyclic, polycarboxylic acids can have the following composition on a moisture-free basis.

TABLE I

|  | Weight Percent | |
| --- | --- | --- |
|  | Broad Range | General Range |
| Carbon | 45–95 | 60–92 |
| Hydrogen | 2.5–7 | 4–6 |
| Oxygen | 2–45 | 3–25 |
| Nitrogen | 0.75–2.5 | 0.75–2.5 |
| Sulfur | 0.3–10 | 0.5–6 |

The carbon and hydrogen content of the coal is believed to reside primarily in multi-ring aromatic compounds (condensed and/or uncondensed) heterocyclic compounds, etc. Oxygen and nitrogen are believed to be present primarily in chemical combination, while some of the sulfur is believed to be present in chemical combination with the aromatic compounds and some in chemical combination with inorganic elements associated therewith, for example, iron and calcium.

In addition to the above the coal will also contain solid, primarily inorganic compounds which will not burn, termed "ash", and which are believed to be composed chiefly of compounds of silicon, aluminum, iron and calcium, with smaller amounts of magnesium, titanium, sodium and potassium. The ash content of the coal treated herein will amount to less than about 50 weight percent, based on the moisture-free coal, but in general will amount to about 0.1 to about 30 weight percent, usually about 0.5 to about 20 weight percent.

Anthracitic, bituminous and subbituminous coal lignitic materials and other types of coal products referred to in ASTM D-388 are exemplary of the coals which can be deashed herein. Some of the coals in their raw state will contain relatively large amounts of water. These can be dried prior to use herein if desired. The coal, prior to use, is preferably ground in a suitable manner, for example, in a hammermill, to size such that at least about 50 percent of the coal will pass through a 40-mesh (U.S. Series) sieve.

The first step in the process involves subjecting the coal to oxidation with aqueous nitric acid. Thus, an aqueous coal slurry, containing from about 40 to about 95 weight percent water, preferably about 50 to about 70 weight percent water, is brought in contact with aqueous nitric acid having a concentration of about five to about 90 weight percent, preferably about 10 to about 70 weight percent. What is important is that the resultant mixture contains coal and nitric acid (as 100 percent nitric acid) in a weight ratio of about 1:0.1 to about 1:10, preferably about 1:0.3 to about 1:5.

The resultant mixture is stirred while maintaining the same at a temperature of about 5° to about 200° C., preferably about 50° to about 100° C. and a pressure of about atmospheric (ambient) to about 1000 pounds per square inch gauge (68 kPa), preferably about atmospheric to about 500 pounds per square inch gauge (34 kPa), for about 0.5 to about 15 hours, preferably about two to about six hours. Gaseous nitrogen oxides that may be formed can be removed from the reaction zone as they are formed. If desired, in order to reduce the consumption of nitric acid, the process can be carried out in the additional presence of molecular oxygen wherein the partial pressure of the molecular oxygen can be in the range of about atmospheric to about 1500 pounds per square inch gauge (100 kPa), preferably about atmospheric to about 750 pounds per square inch gauge (50 kPa).

The resulting slurry is then treated to separate the aqueous phase from the solids therein. This can be done mechanically, for example, using a centrifuge or a filter. The filtrate or aqueous phase containing water, nitric acid, sulfuric acid, some of the ash that was present in the coal charge and other oxidation products, is discarded, while the recovered solids are subjected to extraction using one or a combination of solvents. Although relatively common organic polar solvents, such as acetone, methylethylketone, cyclohexanone, methanol, ethanol, normal propanol, isopropanol, tetrahydrofuran, dioxane, can be used, combination of solvents, for example, a mixture containing a ketone, such as acetone, methylethylketone or cyclohexanone and an alcohol, such as methanol, ethanol or isopropanol, a mixture containing a ketone such as methylethylketone, methylisobutylketone or cyclohexanone and water, a mixture containing a ketonic alcohol, such as acetol, diacetone alcohol, 4-hydroxy-2-butanone, 3-hydroxy-2-butanone or 4-hydroxy-2-pentanone and an ether alcohol, such as tetrahydrofurfuryl alcohol or 2-hydroxymethyltetrahydropyran can also be used. In fact, any solvent can be used in such extraction that will dissolve carbonaceous material in said solids but not the ash content thereof. The conditions of extraction are not critical and can be carried out over a wide range, for example, at a temperature of about 20° to about 200° C., preferably about 25° to about 50° C., and a pressure of about atmospheric to about 500 pounds per square inch (34 kPa), preferably about atmospheric to about 100 pounds per square inch gauge (7 kPa). The solid material left behind is believed to be composed essentially of ash.

The solvent can be removed from the extract in any convenient manner, for example by heating at a temperature of about 10° to about 200° C., preferably about 25° to about 100° C., at a pressure of about 10 millimeters of mercury to about atmospheric, preferably about 100 millimeters of mercury to about atmospheric. Upon removal of the solvent from the extract a solid product composed of substantially water-insoluble polycyclic, polycarboxylic acids, substantially ash and sulfur-free, is obtained. A procedure that can be used to obtain the above-defined material is exemplified in U.S. Pat. No. 4,052,448 to Schulz et al.

The mixture of polycylic, polycarboxylic acids so obtained can be used as such in a furnace or a combustion engine by burning the same therein. The combustion engine that can be used includes internal combustion engines, such as a Diesel engine or a turbine, or an external combustion engine, such as a steam engine. Alternatively, the mixture can be used to prepare a novel fuel composition for use in a furnace or a combustion engine. In one embodiment, the mixture can be dissolved in an alcohol, such as methanol, ethanol, normal propanol, or isopropanol wherein the mixture of acids can amount to about five to about 75 weight percent, preferably about 10 to about 50 weight percent, of the final solution. Alternatively, a slurry can be prepared that includes said mixture and a hydrocarbon fuel wherein the mixture of acids can amount to about five to about 75 weight percent, preferably about 10 to about 60 weight percent, of the final slurry. By "hydrocarbon fuel" we mean to include liquid hydrocarbons, including petroleum fractions, oils resulting from coal liquefaction or other coal conversion processes, the extract from oil shale and tar sands, liquids resulting from the pyrolysis of organic matter, etc. If the extraction is carried out using one of said alcohols, and a fuel is desired containing one of said alcohols, obviously there is no need to separate the alcohol from the extract. The only adjustment that need be made is to obtain proper balance between the extract and the alcohol in the final fuel.

The advantages of the above are many. A fuel is provided that can be burned with no appreciable ash formation and with substantially reduced sulfur pollution. Since substantially all of the ash will be removed from the coal at the plant site, the cost of transporting fuel will be correspondingly reduced. Since the ash-free product used herein can be dissolved in an alcohol or slurried with a hydrocarbon fuel to prepare a fluid, handling or movement thereof over the original raw coal is facilitated.

EXAMPLE I

In this Example a raw Bell Ayr coal having a heat value of 10,154 BTU/pounds (5640 calories/gram) and analyzing as follows, in weight percent on a dry basis, was used: 72.17 percent carbon, 4.74 percent hydrogen, one percent nitrogen, 13.85 percent oxygen, 0.56 percent sulfur and 7.71 weight percent ash. Into an open one-gallon (3850 cc.) glass vessel, equipped with a stirrer, thermometer and heating and cooling coils were introduced 320 cc. of water and 100 cc. of 70 percent aqueous nitric acid. While the contents were stirred, they were brought to 80° C. Over a period of 1.75 hours there was gradually added to the vessel 800 grams (648 grams on a dry basis) of the above coal in powdered form. Over the same 1.75 hours there was also added a mixture containing 302 cc. of water and 298 cc. of 70 percent aqueous nitric acid. Over an additional period of 0.15 hour there was added a mixture containing 18 cc. of water and 17 cc. of 70 percent aqueous nitric acid. The contents of the vessel were then held at 80° C. for 45 minutes. Addition was resumed, lasting for 1.85 hours, of a mixture containing 320 cc. of water and 315 cc. of 70 percent aqeuous nitric acid. The contents of the reaction were then held at 80° C. for one hour, after which they were cooled to room temperature and filtered. The solids obtained were extracted at 87° C. with a two-liter mixture containing 90 weight percent methylethylketone and 10 weight percent water. After removing the solvent from the extract by heating at a temperature of 50° C. there was recovered 512.7 grams of solids whose ash contents was nil and whose sulfuric content was 0.3 weight percent. The heating value of this product was 8673 BTU/pound (4818 calories/gram). The insoluble residue obtained, amounting to 88.2 grams consisted essentially of ash and of insoluble carbon.

From the above it can be seen that at the expense of reducing the caloric content of the coal only about 15 percent a fuel is available possessing no appreciable ash content and posing no sulfur pollution problems.

EXAMPLE II

In this Example a raw Kentucky No. 9 coal having a heat value of 11874 BTU/pound (6956 calories/gram) and analyzing as follows, in weight percent on a dry basis, was used: 68.69 percent carbon, 4.88 percent hydrogen, 1.52 percent nitrogen, 13.17 percent oxygen, 4.39 percent sulfur and 10.9 percent ash. Into an open one-gallon (3850 cc) glass vessel, equipped with a stirrer, thermometer and heating and cooling coils were introduced 320 cc of water and 100 cc of 70 percent aqueous nitric acid. While the contents were stirred, they were brought to 80° C. Over a period of 1.75 hours there was gradually added to the vessel 800 grams (791 grams on a dry basis) of the above coal in powdered form. Over the same 1.75 hours there was also added a mixture of 280 cc of water and 348 cc of 70 percent aqueous nitric acid. Over an additional period of 0.25 hour there was added a mixture containing 40 cc of water and 50 cc of 70 percent aqueous nitric acid. The contents of the vessel were then held at 80° C. for one hour. Addition was resumed, lasting for two hours, of a mixture containing 320 cc of water and 395 cc of 70 percent aqueous nitric acid. The contents of the reactor were held at 80° C. for one hour, after which they were cooled to room temperature and filtered. The solids obtained were extracted at 87° C. with a a two-liter mixture containing 90 weight percent methylethylketone and 10 weight percent water. After removing the solution from the extract by heating at a temperature of 50° C. there was recovered 359 grams of solids whose ash content was nil and whose sulfur content was 1.48 percent. The heating value of this product was 9920 BTU/pound (5511 calories/gram).

The insoluble residue obtained, amounting to 500 grams, consisted essentially of ash and insoluble carbon.

EXAMPLE III

Into a one-gallon (3850 cc) stainless steel autoclave equipped with a stirrer and heating and cooling means there was added 800 grams of powdered lignite (536 grams on a water-free basis) and 640 milliliters of water. The lignite was a North Dakota lignite analyzed, on a moisture-free basis, as follows: 68.2 percent carbon, 4.15 weight percent hydrogen, 16.5 weight percent oxygen, 0.84 weight percent sulfur, 0.93 weight percent nitrogen, and 9.0 weight percent ash. After the contents were heated to 80° C. with stirring, the autoclave was pressured to 450 pounds per square inch gauge (30 kPa) with molecular oxygen. Thereupon 600 cc of 70 percent aqueous nitric acid was added to the reactor over a two-hour period. The contents were then held at the above pressure and above temperature for three hours, after which they were cooled to room temperature, filtered and extracted with two liters of acetone at 50° C. Upon removal of the acetone from the extract there was recovered 354.4 grams of ash-free material. The material insoluble in acetone, amounting to 95.6 grams, was found to be substantially solely ash and insoluble carbonaceous material.

A series of experiments was conducted in which a single cylinder Series D, Witte engine was powered with methanol alone or with combinations of methanol with varying amounts of polycyclic, polycarboxylic acids obtained in this Example III. In each run the engine was started with normal Diesel fuel. After about five minutes of operation in this mode injection of Diesel fuel was discontinued and operation was switched over to the test fuel. Injection of methanol alone repeatedly stalled the engine. A six percent solution of the polycyclic, polycarboxylic acids in methanol, however, when injected into the engine, resulted in smooth operation under full load. A liquid mixture of 60 percent polycyclic, polycarboxylic acids and 40 percent methanol powered the same engine equally well under full load, providing a clean exhaust free of smoke and particulate ash.

Obviously, many modifications and variations of the invention, as hereinabove set forth, can be made without departing from the spirit and scope thereof, and only such limitations should be imposed as are indicated in the appended claims.

We claim:

1. Process for operating a furnace or a combustion engine which comprises burning in said furnace or said combustion engine a mixture of polycyclic, polycarboxylic acids obtained by oxidizing coal with aqueous nitric acid, separating from the resulting product an aqueous phase and a solid phase and then extracting the solid phase with a solvent to recover said mixture.

2. The process of claim 1 wherein the coal being oxidized is in an aqueous slurry containing from about 40 to about 95 weight percent water.

3. The process of claim 1 wherein the coal being oxidized is in an aqueous slurry containing from about 50 to about 70 weight percent water.

4. The process of claim 1 wherein the nitric acid has a concentration of about five to about 90 percent.

5. The process of claim 1 wherein the nitric acid has a concentration of about 10 to about 70 percent.

6. The process of claim 1 wherein the oxidation is carried out at a temperature of about 5° to about 200° C. and a pressure of about atmospheric to about 1000 pounds per square inch gauge over a period of about 0.5 to about 15 hours.

7. The process of claim 1 wherein the oxidation is carried out at a temperature of about 50° to about 100° C. and a pressure of about atmospheric to about 500 pounds per square inch gauge over a period of about two to about six hours.

8. The process of claim 1 wherein said separation is effected by filtration.

9. The process of claim 1 wherein said extraction is carried out using a solvent that will dissolve carbonaceous material in said solid phase.

10. The process of claim 1 wherein said extraction is carried out using a polar solvent.

11. The process of claim 1 wherein said extraction is carried out using at least one solvent selected from the group consisting of acetone, methylethylketone, cyclohexanone, methanol, ethanol, normal propanol, isopropanol, tetrahydrofuran, dioxane, acetol, diacetone alcohol, 4-hydroxy-2-butanone,3-hydroxy-2-butanone, 4-hydroxy-2-pentanone, tetrahydrofurfuryl alcohol and 2-hydroxymethyltetrahydrofuran.

12. The process of claim 1 wherein said extraction is carried out using acetone.

13. The process of claim 1 wherein said extraction is carried out using methylethylketone.

14. The process of claim 1 wherein said burning is effected in a furnace.

15. The process of claim 1 wherein said burning is effected in an internal combustion engine.

16. The process of claim 1 wherein said burning is effected in an external combustion engine.

17. The process of claim 1 wherein said burning is effected in a Diesel engine.

18. The process of claim 1 wherein said burning is effected in a turbine.

19. The process of claim 1 wherein the fuel comprises a (1) a mixture of said polycyclic, polycarboxylic acids and (2) an organic component selected from the group consisting of methanol, ethanol, normal propanol, isopropanol and a liquid hydrocarbon fuel.

20. The process of claim 19 wherein said organic component is methanol.

21. The process of claim 19 wherein said organic component is ethanol.

22. The process of claim 19 wherein said organic component is a liquid hydrocarbon fuel.

23. The process of claim 19 wherein said burning is effected in a furnace.

24. The process of claim 19 wherein said burning is effected in an internal combustion engine.

25. The process of claim 19 wherein said burning is effected in an external combustion engine.

26. The process of claim 19 wherein said burning is effected in a Diesel engine.

27. The process of claim 19 wherein said burning is effected in a turbine.

* * * * *